United States Patent [19]

Greco et al.

[11] 4,092,357

[45] May 30, 1978

[54] PRODUCTION OF PERCHLOROMETHYL MERCAPTAN

[75] Inventors: Carl C. Greco, Garnerville; Edward N. Walsh, New City, both of N.Y.

[73] Assignee: Stauffer Chemical Company, Westport, Conn.

[21] Appl. No.: 753,133

[22] Filed: Dec. 22, 1976

[51] Int. Cl.$^2$ .............................................. C07C 145/00
[52] U.S. Cl. ............................... 260/543 H; 260/664
[58] Field of Search ................................. 260/543 H

[56] References Cited

U.S. PATENT DOCUMENTS

| | | | |
|---|---|---|---|
| 2,545,285 | 3/1951 | Kamlet | 260/543 H |
| 2,575,290 | 11/1951 | Ohsol et al. | 260/543 H |
| 2,647,143 | 7/1953 | Pitt et al. | 260/543 H |
| 2,666,081 | 1/1954 | Churchill | 260/543 H |
| 2,759,969 | 8/1956 | Jonas | 260/543 H |
| 3,014,071 | 12/1961 | Hogt et al. | 260/543 H |
| 3,673,246 | 6/1972 | Meyer et al. | 260/543 H |
| 3,808,270 | 4/1974 | Rupp et al. | 260/543 H |
| 3,878,243 | 4/1975 | Zupanac | 260/543 H |
| 3,968,155 | 7/1976 | Gueren | 260/543 H |
| 3,993,693 | 11/1976 | Blintam | 260/543 H |

FOREIGN PATENT DOCUMENTS

| | | | |
|---|---|---|---|
| 508,163 | 12/1954 | Canada | 260/543 H |
| 1,437,908 | 3/1966 | France | 260/543 H |

OTHER PUBLICATIONS

Sosnovsky, "Chem. Reviews", vol. 58, pp. 509–512 (1958).

*Primary Examiner*—Norman Morgenstern
*Attorney, Agent, or Firm*—Charles B. Rodman; Roger S. Benjamin

[57] ABSTRACT

A method for improving the yield of perchloromethyl mercaptan by including in the reaction mixture amounts of difunctional carbonyl compounds effective to suppress the formation of undesirable byproducts, such as carbon tetrachloride and sulfur monochloride.

8 Claims, No Drawings

PRODUCTION OF PERCHLOROMETHYL MERCAPTAN

BACKGROUND OF THE INVENTION

This invention relates to improvements in the production of perchloromethyl mercaptan. More particularly, it relates to the use of carbonyl compounds as additives which serve to improve the yield of perchloromethyl mercaptan.

Perchloromethyl mercaptan, $Cl_3CSCl$, also known as trichloromethanesulfenyl chloride, has commercial importance as an intermediate in the manufacture of fungicides, bactericides, germicides, herbicides, soil fumigants and pharmaceuticals.

Perchloromethyl mercaptan was first described in a production scheme by Rathke in Annalen, Volume 167, at page 195 (1873). Rathke's method, which is still in use today, utilizes an iodine catalyst. The reaction scheme operates most efficiently at temperatures below about 40° C., in accordance with the following equations:

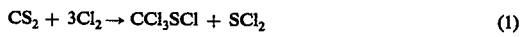

$$CS_2 + 3Cl_2 \rightarrow CCl_3SCl + SCl_2 \quad (1)$$

$$2CS_2 + 5Cl_2 \rightarrow 2CCl_3SCl + S_2Cl_2 \quad (2)$$

$$CS_2 + 3Cl_2 \rightarrow CCl_4 + S_2Cl_2 \quad (3)$$

In addition to sulfur dichloride, sulfur chloride (also known as sulfur monochloride) and carbon tetrachloride, the reaction can also form thiophosgene and other compounds as unwanted byproducts. Although more volatile byproducts such as carbon tetrachloride and sulfur dichloride can be removed from the reaction mixture by distillation, it is extremely difficult to separate perchloromethyl mercaptan from sulfur chloride by this method. This is due to the fact that the boiling points of perchloromethyl mercaptan and sulfur chloride are very close to each other.

The prior art has proposed several methods for improving the basic Rathke method. For example, U.S. Pat. No. 3,544,625 to Masat, discloses a method for producing perchloromethyl mercaptan by chlorinating carbon disulfide in the presence of a solution of inorganic acids, such as hydrochloric acid. U.S. Pat. No. 3,673,246 to Meyer et al., discloses a continuous process for producing perchloromethyl mercaptan wherein carbon disulfide is reacted with chlorine on or in intimate contact with activated carbon at temperatures of about −5° C. to +100° C. U.S. Pat. No. 3,808,270 to Rupp et al., discloses a continuous process for producing perchloromethyl mercaptan by reacting carbon disulfide and chlorine in a reaction zone filled with granular active carbon completely immersed in the liquid reaction mixture while maintaining temperatures in the range of about 40° C. to about 135° C. U.S. Pat. No. 3,878,243 To Zupancic discloses a homogeneous catalyst system comprising a lead salt of a carboxylic acid which is soluble in carbon disulfide.

Notwithstanding the effectiveness of the above prior art patents as methods for producing perchloromethyl mercaptan (PMM), they do not deal with preventing the tendency of PMM to react with chlorine or sulfur dichloride, to form carbon tetrachloride, sulfur, and sulfur monochloride. Mixtures of carbon disulfide, sulfur dichloride and perchloromethyl mercaptan also react in a similar fashion. The reactions which form carbon tetrachloride are believed to be accelerated by trace amounts of metals, such as iron, tin, and bronze, in the reaction mixture.

Small quantities of iron are generally present in the commercial carbon disulfide and chlorine used as reactants for PMM, at levels on the order of parts per million. The chlorine can be treated by passing it through a glass wool filter to remove most of the iron. However, the presence of iron at levels as low as one part per million can be deleterious and capable of effecting significant reductions in the yield of perchloromethyl mercaptan. It has, therefore, been an objective of industry to develop agents capable of ameliorating the effect of metallic impurities present in the reactants and/or catalyst, so that the formation of carbon tetrachloride, sulfur monochloride and other undesirable byproducts is suppressed.

Another problem in the production of perchloromethyl mercaptan occurs in the decomposition of sulfur dichloride to sulfur chloride and chlorine in the following manner:

$$2SCl_2 \rightleftharpoons S_2Cl_2 + Cl_2 \quad (4)$$

This reaction is undesirable due to the fact that the boiling points of perchloromethyl mercaptan and sulfur chloride are so close to each other that it is impractical to separate them by distillation. Thus, it has also been an objective of industry to develop agents for stabilizing sulfur dichloride to thereby prevent it from forming sulfur chloride and chlorine.

The present invention has achieved improvements in the production of perchloromethyl mercaptan via the use of carbonyl compounds as additives which are believed to suppress the formation of the undesirable byproducts occurring in reactions (3) and (4).

DESCRIPTION OF THE PREFERRED EMBODIMENT

In accordance with the present invention, improved yields of perchloromethyl mercaptan have been achieved by the addition of small amounts of carbonyl compounds to the reaction system.

The carbonyl compounds that have been found to be most effective in accomplishing the purposes of the present invention are difunctional in nature and have the following generic formulae:

$$R-\underset{\underset{O}{\|}}{C}-(CX_2)_n-\underset{\underset{O}{\|}}{C}-R \quad (A)$$

$$R-\underset{\underset{O}{\|}}{C}-(CX_2)_n-\underset{\underset{OR'}{|}}{C}H-R \quad (B)$$

wherein R independently is a hydrocarbyl, alkoxy, or substituted hydrocarbyl group; R' independently is an alkyl group or hydrogen; and X independently is hydrogen or a halogen; and n is an integer varying from 0 to 3.

Typical examples of hydrocarbyl groups are alkyl, cycloalkyl, aralkyl, alkaryl, and aryl, with the alkyl groups having from 1 to about 20 carbon atoms, and preferably from 1 to about 10 carbon atoms. The alkyl groups can be straight, branch chained or cyclic.

Typical examples of substituted alkyl and substituted aryl as used herein are meant to designate alkyl or aryl groups having attached thereto at least one substituent of the type: halogen, cyano, carboxyl, carboxylate, amido, amino, nitro, hydroxy or alkoxy, with the proviso that the substituents not adversely affect the preparation of perchloromethyl mercaptan. The preferred substituents are halogen, and most preferably, chlorine.

A typical aryl group can be phenyl and the like. Typical alkaryl groups can be cresyl, xylyl and the like, and aralkyl can be benzyl and the like. Typical examples of the preferred difunctional carbonyl compounds and their derivatives, found to be especially effective in increasing the yield of perchloromethyl mercaptan are the alkyl diones having from about 4 to about 10 carbon atoms, such as the butanediones, pentanediones, hexanediones, heptanediones, octanediones, nonanediones, decanediones, mixtures thereof, and their isomers.

The addition of the difunctional carbonyl compounds to the reactants involved in the production of perchloromethyl mercaptan is accomplished most effectively by contacting the additives in situ with carbon disulfide and the catalyst, followed by contacting with chlorine over an extended period of time while maintaining the reaction temperature in accordance with the particular catalyst system utilized, and mode of production for the PMM.

It should be noted that the reaction temperatures required for batch process production of PMM are generally lower than the temperatures which can be maintained in a continuous process. For example, batch process temperatures generally vary from about 10° C. to about 40° C., when using a carbon or iodine catalyst. At above about 40° C. in a batch process, PMM would tend to decompose into $CCl_4$ and $S_2Cl_2$. The iodine catalyzed system is preferably run below 40° C. in either a batch or continuous reaction. The carbon catalyzed system can operate in a continuous mode at temperatures above 40° C. if done in accordance with U.S. Pat. No. 3,808,270.

The difunctional carbonyl compounds are generally added in amounts which vary from about 0.01 to about 10%, and preferably from about 0.1 to about 5% by weight of the carbon disulfide feed. Larger amounts can be used, however, no advantage is accrued thereby. In general, it has been found that use of the difunctional carbonyl compounds in the stated manner significantly reduces the formation of carbon tetrachloride and other unwanted byproducts, and increases the yield of perchloromethyl mercaptan to yields as high as 95%, based upon the chlorine reacted.

In the examples which follow, all parts and percentages are by weight unless otherwise specified.

EXAMPLES 1-9

In a 250 milliliter glass jacketed flask fitted with a chlorine inlet tube, dry ice condenser and mechanical stirrer, 76 grams (1 mole) of carbon disulfide and 0.3 grams of iodine were contacted with 0.5 grams of 2,3-hexanedione. This mixture was then contacted with 182 grams (2.6 moles) of chlorine bubbled in over a 4½ hour period. During the chlorine contacting, the reaction temperature was maintained with outside cooling at a temperature varying from about 20° to about 24° C. the reaction mixture was then vacuum distilled at temperatures ranging from 70° C. to 100° C. at 200 mm. of mercury. 141.4 grams (0.76 moles) of perchloromethyl mercaptan were obtained. This is an 89% yield based upon the chlorine reacted. The above procedure was repeated successively, except for the use of different difunctional carbonyl additives. The results are tabulated below:

| Ex. | Additive | Amount, Grams | PMM Yield % |
|---|---|---|---|
| 2 | Ethyl acetoacetate $CH_3C-CH_2C-CH_2CH_3$ with $\underset{O}{\|\|}$ $\underset{O}{\|\|}$ | 0.5 | 82 |
| 3 | Diethyl malonate $CH_3CH_2OCCH_2COCH_2CH_3$ with $\underset{O}{\|\|}$ $\underset{O}{\|\|}$ | 0.5 | 86 |
| 4 | Dimethyl oxalate $CH_3OC-COCH_3$ with $\underset{O}{\|\|}$ $\underset{O}{\|\|}$ | 0.5 | 83 |
| 5 | Acetyl acetaldehyde dimethyl acetal $CH_3C-CH_2-CHOCH_3$ with $\underset{O}{\|\|}$ $\underset{OCH_3}{\|}$ | 0.5 | 85 |
| 6 | Acetylacetone $CH_3C-CH_2-C-CH_3$ with $\underset{O}{\|\|}$ $\underset{O}{\|\|}$ | 0.5 | 91 |
| 7 | Acetylacetone | 0.1* | 93 |
| 8 | Benzoin $\phi-C(=O)-CH(OH)-\phi$ | 0.5 | 85 |
| 9 | — | — | 80 |

*0.2 g of iodine used

EXAMPLE 10

76 grams (1 mole) of carbon disulfide, 28 grams of charcoal (CXAL coconut charcoal from Union Carbide) and 0.5 grams of acetylacetone were placed into a 250 ml. glass jacketed flask fitted with a chlorine inlet tube, dry ice condenser and mechanical stirrer. Thermostated water (25° C) was continuously cycled thru the reactor jacket. The solution was stirred and 182.0 grams (2.6 moles) of chlorine was bubbled through the reaction mixture over a 4 hour period. A total of 198 grams of liquid was separated from the charcoal by vacuum distillation at temperatures ranging from 70° C. to 100° C. under a vacuum ranging from 50 to 60 mm. Hg. A total of 119 grams was obtained as a distillate, 74 grams as a dry ice trap condensate, and an additional 5 grams were obtained by washing the charcoal with chloroform. Analysis of the various fractions of liquid indicated a yield of 122 grams of PMM, which is a 78% yield based on the chlorine reacted. The yield of side product $CCl_4$ was 2% of theory.

EXAMPLE 11

The same procedure as Example 10 was repeated without an additive. After the reaction was completed, 219 grams of liquid were obtained comprising 128 grams of distillate, 85 grams as a dry ice trap condensate and 5.7 grams obtained by washing the charcoal with chloroform. Analysis of the various fractions by gas chromatography indicated a yield of 128.5 grams of PMM which is a 69% yield based on the chlorine reacted and a 19% yield of $CCl_4$.

What is claimed is:

1. In a method for producing perchloromethyl mercaptan via the catalytic reaction of chlorine and carbon disulfide, the improvement which comprises contacting the reactants with difunctional carbonyl compounds having the following structure:

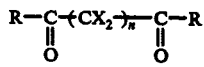

OR

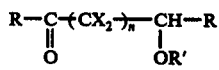

wherein R independently is a hydrocarbyl, alkoxy, or substituted hydrocarbyl group; R' independently is an alkyl group or hydrogen; and X independently is hydrogen or a halogen; and $n$ is an integer varying from 0 to 3, wherein said carbonyl compounds are added in amounts effective to suppress the formation of carbon tetrachloride and sulfur monochloride.

2. In a method for producing perchloromethyl mercaptan via an iodine catalyzed reaction of chlorine and carbon disulfide, the improvement which comprises contacting the reactants with difunctional carbonyl compounds having the following structure:

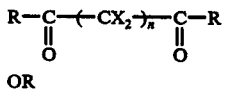

OR

-continued

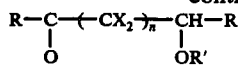

wherein R independently is a hydrocarbyl, alkoxy, or substituted hydrocarbyl group; R' independently is an alkyl group or hydrogen; and X independently is hydrogen or a halogen; and $n$ is an integer varying from 0 to 3, wherein said carbonyl compounds are added in amounts which vary in the range of from about 0.01 to about 10% by weight of the carbon disulfide feed so as to suppress the formation of carbon tetrachloride and sulfur monochloride.

3. The method of claim 1 wherein said carbonyl compounds are alkyl diones having from about 4 to about 10 carbon atoms.

4. The method of claim 1 wherein said carbonyl compounds are added in amounts which vary from about 0.01 to about 10% by weight of the carbon disulfide feed.

5. The method of claim 4 wherein said carbonyl compounds vary from about 0.1 to about 5% by weight of the carbon disulfide feed.

6. The method of claim 1 wherein said catalyst is iodine.

7. The method of claim 1 wherein said catalyst is activated carbon.

8. The method of claim 1 wherein said catalyst is a lead salt.

* * * * *